United States Patent [19]

Kim

[11] Patent Number: 5,190,757

[45] Date of Patent: * Mar. 2, 1993

[54] PHARMACEUTICAL LIQUID COMPOSITION CONTAINING BEZOAR BOVIS AND PREPARATION FOR ITS MANUFACTURE

[76] Inventor: Young S. Kim, Cosmos Mansion #1002, 302-62 Ichon-Dong, Yongsan-Ku, Seoul, Rep. of Korea

[*] Notice: The portion of the term of this patent subsequent to Nov. 17, 2009 has been disclaimed.

[21] Appl. No.: 595,673

[22] Filed: Oct. 11, 1990

Related U.S. Application Data

[63] Continuation of Ser. No. 275,725, Nov. 23, 1988, abandoned.

[30] Foreign Application Priority Data

May 16, 1988 [KR] Rep. of Korea ...................... 88-5668

[51] Int. Cl.[5] .............................................. A61K 35/78
[52] U.S. Cl. .................................. 424/195.1; 424/520; 424/551
[58] Field of Search ....................... 424/195.1, 520, 551

[56] References Cited

PUBLICATIONS

Steinmetz, Codex Vegetabilis, ref. Nos. 99, 209, 304, 403, 524-525, 788-789, 800, 907, 1042, 1215-1216 (1957).

*Primary Examiner*—John W. Rollins
*Attorney, Agent, or Firm*—Birch, Stewart, Kolasch & Birch

[57] ABSTRACT

A pharmaceutical liquid composition prepared by combining a predetermined quantity of natural substances from the genera Glycyrrhizae Radix, Ginseng Radix, Typhae Pollen, Massa Medicata Fermentata, Sojae germinatum Semen, Cinnamomi Cortex, Gelatin, Paeoniae Radix, Liriope Tuber, Scutellariae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Ampelopsis Radix, Zingiberis Rhizoma, Dioscoreae Rhizoma, Cinnabaris, Realgar, Aurum, and Mel and cutting the natural substances into microparticle size or extracting the natural substances with water to form a first product; providing a predetermined quantity of natural substances from the genera Bezoar Bovis, Moschus, and Rhinocerotis; cutting the natural substances into a microparticle size and extracting with water or alcohol to form a second product; providing a genus Gelatin solution; providing a genus Borneol solution; mixing the first and second products and the Gelatin and Borneol solutions to form a mixture; and preparing the mixture with water to produce a pharmaceutical liquid composition for orally administering to patients such as infants, children, critical patients, and the like.

4 Claims, No Drawings

PHARMACEUTICAL LIQUID COMPOSITION CONTAINING BEZOAR BOVIS AND PREPARATION FOR ITS MANUFACTURE

This application is a continuation of application Ser. No. 07/275,725 filed on Nov. 23, 1988 which is now abandoned.

BACKGROUND OF THE INVENTION

1. Field of the Invention

The present invention relates generally to a novel pharmaceutical liquid composition containing Bezoar Bovis for treating patients suffering from stroke, arteriosclerosis, hypertension, tachycardia, dyspnea, anxiety, cardiostenosis, acute and chronic convulsion, automatic nervous system disease, and coma, and to a preparation method for its manufacture. More particularly, the present invention relates to the preparation of oral and parental natural substance liquids of improved physical stability.

2. Description of the Prior Art

The only known prior art of solid composition preparations obtained from natural substances is found in "Annals of Oriental Medicine" by Joon Huh. This publication discloses a solid Bezoar Bovis pill containing 45 mg of Bezoar Bovis, 187.5 mg of Glycyrrhizae Radix, 93.7 mg of Ginseng Radix, 93.7 mg of Typhae Pollen, 93.7 mg of Massa Medicata Fermentata, 65.6 mg of Sojae germinatum Semen, 65.6 mg of Cinnamomi Cortex, 65.6 mg of Gelatin, 56.2 mg of Paeoniae Radix, 55.6 mg of Liriopsis tuber, 56.2 mg of Scutellariae Radix, 56.2 mg Angelicae Gigantis Radix, 56.2 mg of Ledebouriellae Radix, 56.2 mg of Atractylodis Rhizoma Alba, 46.8 mg of Bupleuri Radix, 46.8 mg of Platycodi Radix, 46.8 mg of Armeniacae Semen, 46.8 mg Hoelen, 46.8 mg of Cnidii Rhizoma, 37.5 mg of Antellopis Cornu, 37.5 mg of Moschus, 37.5 mg of Borneol, 28.1 mg of Ampelopsis Radix, 28.1 mg of Zingiberis Rhizoma, 75 mg of Rhinocerotis, 56.2 mg of Cinnabaris, 30 mg of Realgar, a piece of Aurum, 2 grains of Zizyphi Fructus, and QS (Quantum Sufficit) of Mel. However, since the Cinnabaris possesses a heavy metal toxicity, the present time, a modified prescription of the solid Bezoar Bovis pill discloses that at least one of the following substances does not include in the solid Bezoar Bovis pill. That is, Ginseng Radix, Sojae germinatum Semen, Cinnamomi Cortex, Angelicae Gigantis Radix, Ampelopsis Radix, Zingiberis Rhizoma, Rhinocerotis, Cinnabaris, Realgar, Aurum, Zizyphi Fructus, and Mel does not include in the modified prescription of the solid Bezoar Bovis pill. For example, a modified prescription of the solid Bezoar Bovis pill does not include Ginseng Radix, .Sojae germination Semen, Cinnamomi Cortex, Angelicae Gigantis Radix, Ampelopsis Radix, Zingiberis Rhizoma, Rhinocerotis, Gelatin, Cinnabaris, and Realgar. Another modified prescription of the solid Bezoar Bovis pill does not include Cinnabaris, Realgar, Zizyphi Fructus, and Mel. A further modified prescription of the solid Bezoar Bovis pill does not include Rhinocerotis, Cinnabaris, Aurum, and Zizyphi Fructus. These modified prescription of the solid Bezoar Bovis pill is still used in cleaning a patient's chest. However, such prior art Bezoar Bovis pills suffer from many disadvantages such as, for example, it is not feasible for patients in critical condition to orally and parentally administer these pills nor is it feasible for infants and children to orally and parentally administer them. Furthermore, these pills do not provide for treatment of the illness of a patient in a fast manner.

SUMMARY OF INVENTION

Accordingly, it is an object of the present invention to provide a pharmaceutical liquid composition such as gel or sol preparation which is a mixture of natural substances including Bezoar Bovis, Dioscoreae Rhizoma, Glycyrrhizae Radix, Ginseng Radix, Typhae Pollen, Massa Medicata Fermentata, Sojae germinatum Semen, Cinnamomi Cortex, Gelatin, Paeoniae Radix, Liriope Tuber, Scutellariae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Moschus, Borneol, Ampelopsis Radix, Zingiberis Rhizoma, Rhinocerotis, Cinnabaris, Realgar, Aurum, Zizyphi Fructus, and Mel for easy oral and parenteral administration thereof to critical patients.

Another object of the present invention is to provide a preparation method of pharmaceutical liquid from the above-identified natural substances or the above-identified natural substances which does not include several substances therefrom for providing medication to infants and children.

A further object of the present invention is to provide a preparation method for manufacturing a pharmaceutical liquid composition containing ox Bezoar Bovis for cleaning a patient's chest.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

The present invention pertains to a pharmaceutical liquid composition prepared by a process which comprises providing a predetermined quantity of natural substances from the genera Dioscoreae Rhizoma, Glycyrrhizae Radix, Ginseng Radix, Typhae Pollen, Massa Medicata Fermentata, Sojae germinatum Semen, Cinnamomi Cortex, Gelatin, Paeoniae Radix, Liriope Tuber, Scutellariae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Moschus, Borneol, Ampelopsis Radix, Zingiberis Rhizoma, Cinnabaris, Realgar, Aurum, Zizyphi Fructus, and Mel; cutting the natural substances into a microparticle size and/or extracting the natural substances with water to form a first extract; providing a predetermined quantity of natural substances from the genera Bezoar Bovis, Moschus, and Rhinocerotis; cutting the natural substances into a microparticle size and mixing the natural substances with ethanol to form a second solution; providing a genus Borneolum solution and a genus Gellatin solution; mixing the first extract with the second solution and the Borneol and Gelatin solutions to form a mixture; and preparing the mixture with water to produce a pharmaceutical liquid composition for orally administering to patients such as infants, children, critical patients, and the like.

DETAILED DESCRIPTION OF PREFERRED EMBODIMENT

Referring now in detail to the present invention, there is provided a pharmaceutical liquid composition, the composition being made from natural substances, namely, the genera Bezoar Bovis, Dioscoreae Rhizoma, Glycyrrhizae Radix, Ginseng Radix, Typhae Pollen, Massa Medicata Fermentata, Sojae germinatum Semen, Cinnamomi Cortex, Gellatin, Paeoniae Radix, Liriope Tuber, Scutellariae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Moschus, Borneol, Ampelopsis Radix, Zingiberis Rhizoma, Rhinocerotis, Cinnabaris, Realgar, Aurum, Zizyphi Fructus, and Mel. Before the cutting or extracting the natural substances, the genera Bezoar Bovis, Dioscoreae Rhizoma, Glycyrrhizae Radix, Ginseng Radix, Typhae Pollen, Massa Medicata Fermentata, Sojae germinatum Semen, Cinnamomi Cortex, Gelatin, Paeoniae Radix, Liriope Tuber, Scutellariae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Moschus, Borneol, Ampelopsis Radix, Zingiberis Rhizoma, Rhino Cerotis, Cinnabaris, Realgar, Aurum, Zizyphi Fructus, and Mel are mixed together in a predetermined weight ratio.

First of all, 450 g of Dioscoreae Rhizoma; 320 g of Glycyrrhizae Radix; 180 g of Cnidii Rhizoma; 160 g of Ginseng Radix, Typhae Pollen, and Massa Medicata Fermentata; 130 g of Sojae germinatum Semen and Cinnamomi Cortex; 120 g of Ledebouriellae Radix; 110 g of Paeoniae Radix, Liriopsis tuber, Scutellariae Radix, Angelicae Gigantis Radix, and Atractylodis Rhizoma Alba; 100 g of Mel; 84 g of Hoelen; 80 g of Bupleuri Radix, Platycodi Radix, and Armeniacae Semen; 65 g of Antellopis Cornu; 46 g of Ampelopsis Radix and Zingiberis Rhizoma; 50 g of Realgar; and 26 g of Aurum and Zizyphi Fructus are cut into microparticle size, extracted with 5 times the volume of water as the mixture for about 2 hours, and filtered to form a first extract and then the filtrate is filtered again after 5 times the volume of water as the filtrate is added into the filtrate.

Secondly, 150 g of Rhinocerotis; 14 g of Bezoar Bovis; and 38 g of Moschus are cut into microparticle size to produce a microparticle product. 5 times the volume of ethanol as the microparticle product is added to the microparticle product for about 10 days, filtered, and concentrated. At this time, the ethanol is recovered, condensed, and reintroduced to the filtrate. 150 g of sodium alginate and 200 g water are added to the condensed solution or the microparticle product to form a second extract or a second solution.

Thirdly, 66 g of Gellatin is added to distilled water at an elevated temperature to produce a Gelatin solution.

Fourthly, 10 g of sugar and 1 Kg of solvitol or ASPARTAME, 3-amino-N-(α-carboxyphenethyl)succinamic acid N-methyl ester, are added to water to form a sweetening solution and is added to the above-produced second extract.

Fifthly, 90 g of Borneol and 5 g of l-methanol are solved in QS of ethanol to form a Burneol solution.

The above-produced first extract, second extract, Borneol solution and Gelatin solution are then mixed together with QS water to be 30 liter of the volume of total mixture solution to produce a pharmaceutical liquid composition for orally administering to patients. At this time, if necessary, a preservative, sweetening agent, stabilizer, solvent, emulsifier, colloidifier, aromatic agent, or the like can be added and mixed with the above-resulted liquid composition.

The various species of the genera of natural substances found to be useful for the pharmaceutical composition of the present invention are *Bos taurus* var domesticus Gmelin of Bezoar Bovis, *Glycyrrhiza glabra* Linne var grandifera or *Glycyrrhiza uratensis* of Glycyrrhizae Radix, *Panax schinseng* Nees of Ginseng Radix, *Typhar orientalis* presl of Typhae Pollen, *Glycine max* Merril of Sojae germinatum Semen, *Cinnamomum cassia* of Cinnamomi Cortex, *Paeonia albiflora pallas* var. trichocarpa of Paeoniae Radix, *Liriope platyphylla* Wang at Tang of Liriope Tuber, *Scutellaria baicalensis* Georgi of Scutellariae Radix, *Angelica gigas* Nakai of Angelical Gigantis Radix, *Ledebouriella seseloides* Wolff of Ledebouriellae Radix, *Atractylodes japonica* Koidzumi of Atractylodis Rhizoma Alba, *Bupleurum falcatum* Linne of Bupleuri Radix, *Platycodon grandiflorum* A de Candolle of Platycodi Radix, *Prunus armeniaca* Linne var. ansu Maximowicz or *P. mandshurica* Kochne var. glabra Nakai of Armeniacae Semen, *Poria cocos* Wolf of Hoelen, *Cnidium officinale* Makino of Cnidii Rhizoma, *Gazella subgutturosa* Guldenstaedt of Antellopis Cornu, *Moschus moschiferus* Linne of Moschus, *Dryobalanops aromatica* Gaertner of Borneol, *Ampelopsis japonica* Makino of Ampelopsis Radix, *Zingiber officinale* Roscoe of Zingiberis Rhizoma, *Dioscorea japonica* Thumberg of Dioscoreae Rhizoma, *Rhinocerotus biornis* Linne of Rhinocerotis, Cinnabaris, Realgar, Aurum, and *Zizyphus vulgaris* Lamark of Zizyphi Fructus.

Preservatives useful according to the present invention include p-oxybenzoic propyl ester (propyl-p-ben) p-oxybenzoic methyl ester (methyl-p-ben), sodium phosphoric benzoate, and the like.

Sweetening agents useful in accordance with the present invention include honey, sugar, sorbitol, saccharine, ASPARTAME, 3-amino-N-(α-carboxyphenethyl-succinamic acid N-methyl ester, and the like.

Solvents useful for the present invention include distilled water, ethanol, and the like.

Colloidal agents and emulsifiers which may be used include sodium carboxymethylcellulose, pectin, agar, alganic acid, and the like.

Useful aromatic agents include menthol, cinnamomi cortex, orange perfume, and the like.

The present invention will now be described in more detail in connection with the following examples which should be considered as being exemplary and not limiting the present invention.

EXAMPLE 1

263 g of Dioscoreae Rhizoma; 188 g of Glycyrrhizae Radix; 94 g of Ginseng Radix, Typhae Pollen, and Massa Medicata Fermentata; 66 g of Sojae germinatum Semen and Cinnamomi Cortex; 56 g of Paeoniae Radix, Liriope Tuber, Scutellariae Radix, Angelicae Gigantis Radix, Ledebouriellae Radix, and Atractylodis Rhizoma Alba; 47 g of Bupleuri Radix, Platycodi Radix, Armeniacae Semen, Hoelen, and Cnidii Rhizoma; 38 g of Antellopis Cornu; and 28 g of Ampelopsis Radix and Zingiberis Rhizoma are cut into microparticle size by a cutting apparatus. Then 7.5 liters of water are added to approximately 1.5 Kg of the natural substance mixture in an extractor. The mixture in the extractor is stirred and condensed. Thereafter, the aqueous mixture is filtered and residues from the first filtration are extracted with water and are again filtered. Both filtrates are condensed for about 2 hours to produce a natural substance extract.

45 g of Bezoar Bovis; 38 g of Moschus and Borneol; and 300 g of carboxymethylcellulose are ground into microparticle size in a grinder to form a microparticle mixture. Then 200 ml of water are added to the microparticle mixture to produce a Bezoar Bovis solution. 10 Kg of sugar and 1 Kg of sorbitol or 1 Kg of ASPARTAME, 3- amino-N-(α-carboxyphenethyl)succinamic acid N-methyl ester, are solved with QS of distilled water to make a sweetening solution which is added to the Bezoar Bovis liquid to produce a Bezoar Bovis mixture solution.

QS of distilled water is added to 66 g of the genus Gelatin and the aqueous mixture is heated to produce a Gelatin liquid. 38 g of Borneolum and 5 g of l-methanol are added to QS of ethanol to produce a Borneolum solution.

The above-produced products, that is the natural substance extract, the Bezoar Bovis mixture solution, the Gelatin solution, and the Borneol solution are mixed together with QS of distilled water to a 30 liter volume. Thereafter, the mixture is stirred uniformly to produce a pharmaceutical liquid product for orally and parenterally administering to patients. The final pharmaceutical liquid product can be prepared as a gel, sol, or a like preparation for easy administration and so as to simplify packaging.

EXAMPLE 2

The pre-extraction procedures in forming the natural substance mixture in Example 1 are repeated. Then 7.5 liters of ethanol are added to the natural substance mixture at a cold temperature and the extract allowed to stand for about 10 days. The mixture is filtered and QS of distilled water is added to the residues from the first filtration to make again a natural substance extract.

The procedures for making the first and second extracts, and the Bezoar Bovis mixture solution and the Gelatin solution of Example 1 are repeated. The natural substance extract, the Bezoar Bovis mixture solution, and the Gelatin solution are mixed and added to 30 liters of purified water for use as a pharmaceutical, oral liquid.

EXAMPLE 3

The procedures in forming the natural substance mixture as a microparticle size in Example 1 are repeated. The Bezoar Bovis mixture solution, the Gelatin solution and the Borneolum solution in Example 1 are repeated.

The above-produced products, that is, the natural substance, the Bezoar Bovis mixture solution, the Gelatin solution, and the Borneol solution are mixed together with QS of distilled water to a 30 liter volume. Thereafter, the mixture is stirred uniformly to produce a pharmaceutical liquid product for orally and parenterally administering to patients. The final pharmaceutical liquid product can be prepared as a gel, sol, or a like preparation for easy administration and so as to simplify packaging.

EXAMPLE 4

282 g of Dioscoreae Rhizoma; 202 g of Glycyrrhizae Radix; 97 g of Ginseng Radix; 100 g of Typhae Pollen and Massa Medicata Fermentata; 70 g of Sojae germinatum Semen and Cinnamomi Cortex; 60 g of Paeoniae Radix, Liriope Tuber, Scutellariae Radix, Angelicae Gigantis Radix, Ledebouriellae Radix, and Atractylodis Rhizoma Alba; 50 g of Bupleuri Radix, Platycodi Radix, Armeniacae Semen, Hoelen, and Cnidii Rhizoma; 35 g of Antellopis Cornu; and 30 g of Ampelopsis Radix and Zingiberis Rhizoma are cut into microparticle size by a cutting apparatus. Then 7.5 liters of water are added to approximately 1.5 Kg of the natural substance mixture in an extractor. The mixture in the extractor is stirred and condensed. Thereafter, the aqueous mixture is filtered and residues from the first filtration are again filtered. Both filtrates are condensed for about 2 hours to produce a natural substance extract.

14 g of Bezoar Bovis; 5 g of Moschus; 15 g of Rhinocertis; and 300 g of pectin are ground into microparticle size in a grinder to form a microparticle mixture. Then 200 ml of water are added to the microparticle mixture to produce a Bezoar Bovis solution. 10 Kg of sugar and 1 Kg of sorbitol or ASPARTAME, 3-amino-N-(α-carboxyphenethyl)succinamic acid N-methyl ester, are solved with QS of distilled water to make a sweetening solution which is added to the Bezoar Bovis liquid to produce a Bezoar Bovis mixture solution.

QS of distilled water is added to 70 g of the genus Gelatin and the aqueous mixture is heated to produce a Gelatin liquid. 41 g of Borneol and 5 g of l-methanol are added to QS of ethanol to produce a Borneolum solution.

The above-produced products, that is the natural substance extract, the Bezoar Bovis mixture solution, the Gelatin solution, and the Borneol solution are mixed together with QS of distilled water to a 30 liter volume. Thereafter, the mixture is stirred uniformly to produce a pharmaceutical liquid product for orally and parenterally administering to patients. The final pharmaceutical liquid product can be prepared as a gel, sol, or a like preparation for easy administration and so as to simplify packaging.

EXAMPLE 5

131.25 g of Dioscoreae Rhizoma; 93.75 g of Glycyrrhizae Radix; 46.875 g of Ginseng Radix, Typhae Pollen and Massa Medicata Fermentata; 32.75 g of Sojae germinatum Semen and Cinnamomi Cortex; 28 g of Paeoniae Radix, Liriope Tuber, Scutellariae Radix, Angelicae Gigantis Radix, Ledebouriellae Radix, and Atractylodis Rhizoma Alba; 23.25 g of Bupleuri Radix, Platycodi Radix, Armeniacae Semen, Hoelen, and Cnidii Rhizoma; 18.75 g of Antellopis Cornu; Ampelopsis Radix and Zingiberis Rhizoma; 15 g of Realgar; and 12.6 g of Zizyphi Fructus are cut into microparticle size by a cutting apparatus. Then 7.5 liters of water are added to approximately 1.5 Kg of the natural substance mixture in an extractor. The mixture in the extractor is stirred and condensed. Thereafter, the aqueous mixture is filtered and residues from the first filtration are again filtered. Both filtrates are condensed for about 2 hours to produce a natural substance extract.

22.5 g of Bezoar Bovis; 18.75 g of Moschus; 37.5 g of Rhinocertis; 28 g of Cinnabaris; and 100 g of sodium carboxymethylcellulose are ground into microparticle size in a grinder to form a microparticle mixture. Then 200 ml of water are added to the microparticle mixture to produce a Bezoar Bovis solution. 5 Kg of sugar and 2 Kg of sorbitol or ASPARTAME, 3-amino-N-(α-carboxyphenethyl)succinamic acid N-methyl ester, are solved with QS of distilled water to make a sweetening solution which is added to the Bezoar Bovis liquid to produce a Bezoar Bovis mixture solution.

QS of distilled water is added to 32.75 g of the genus Gelatin and the aqueous mixture is heated to produce a Gelatin liquid. 18.75 g of Borneol and 15 g of l-methanol are added to QS of ethanol to produce a Borneol solution.

The above-produced products, that is the natural substance extract, the Bezoar Bovis mixture solution, the Gelatin solution, and Borneol solution are mixed together with QS of distilled water to a 30 liter volume. Thereafter, the mixture is stirred uniformly to produce a pharmaceutical liquid product for orally and parenterally administering to patients. The final pharmaceutical liquid product can be prepared as a gel, sol, or a like preparation for easy administration and so as to simplify packaging.

EXAMPLE 6

450 g of Dioscoreae Rhizoma; 320 g of Glycyrrhizae Radix; 160 g of Ginseng Radix, Typhae Pollen and Massa Medicata Fermentata; 130 g of Sojae germinatum Semen and Cinnamomi Cortex; 110 g of Paeoniae Radix, Liriope Tuber, Scutellariae Radix, Angelicae Gigantis Radix, and Atractylodis Rhizoma Alba; 120 g of Ledebouriellae Radix; 80 g of Bupleuri Radix, Platycodi Radix, Armeniacae Semen; 84 g of Hoelen; 180 g of Cnidii Rhizoma; 65 g of Antellopis Cornu; 46 g of Ampelopsis Radix and Zingiberis Rhizoma; 23 g of Cinnabaris; 50 g of Realgar; 26 g of Aurum, and 100 g of Mel are cut into microparticle size by a cutting apparatus. Then 7.5 liters of water are added to approximately 1.5 Kg of the natural substance mixture in an extractor. The mixture in the extractor is stirred and condensed. Thereafter, the aqueous mixture is filtered and residues from the first filtration are again filtered. Both filtrates are condensed for about 2 hours to produce a natural substance extract.

14 g of Bezoar Bovis; 38 g of Moschus; and 150 g of Rhinocerotis are ground into microparticle size in a grinder to form a microparticle mixture. Then 5 times of the volume of ethanol as the mixture are added to the microparticle mixture to produce a Bezoar Bovis solution. 10 Kg of sugar and 1 Kg of sorbitol or ASPARTAME, 3-amino-N-(α-carboxyphenethyl)succinamic acid N-methyl ester, are solved with QS of distilled water to make a sweetening solution which is added to the Bezoar Bovis liquid to produce a Bezoar Bovis mixture solution.

QS of distilled water is added to 66 g of the genus Gelatin and the aqueous mixture is heated to produce a Gelatin liquid. 90 g of Borneol and 5 g of l-methanol are added to QS of ethanol to produce a Borneol solution.

The above-produced products, that is the natural substance extract, the Bezoar Bovis mixture solution, the Gelatin solution, and Borneol solution are mixed together with QS of distilled water to a 30 liter volume. Thereafter, the mixture is stirred uniformly to produce a pharmaceutical liquid product for orally and parenterally administering to patients. The final pharmaceutical liquid product can be prepared as a gel, sol, or a like preparation for easy administration and so as to simplify packaging.

EXPERIMENT 1

The present Experiment 1 is the data resulting from experimentation of the pharmaceutical liquid according to the present invention. A 30 ml sample prepared from Example 1 is used in the following tests for determining the respective amounts of (a) active bilirubin at a temperature of 30° C. and 60° C. (Table 1), (b) active bilirubin in direct sunlight and in a room wherein the sun rays are scattered (Table 2), and active bilirubin after a long period of storage (Table 3) as follows:

TABLE 1

| Lot No. | Period | Condition 30° C. | | | | | Condition 60° C. | | | | |
|---|---|---|---|---|---|---|---|---|---|---|---|
| | | Result (Remarks) | pH | Density | Viscosity | Content | Result (Remarks) | pH | Density | Viscosity | Content |
| SU-83001 | Beginning | Suitability | 4.819 | 1.130 | 20.62 | 189.6 | Suitability | 4.819 | 1.103 | 20.61 | 189.6 |
| | 2 (Months) | " | 4.818 | 1.131 | 20.61 | 190.1 | " | 4.819 | 1.131 | 20.54 | 189.6 |
| | 4 (Months) | " | 4.817 | 1.130 | 20.64 | 188.6 | " | 4.818 | 1.132 | 20.55 | 188.4 |
| | 6 (Months) | " | 4.816 | 1.132 | 20.65 | 188.2 | " | 4.816 | 1.131 | 20.57 | 187.0 |
| SU-83002 | Beginning | " | 4.821 | 1.130 | 20.52 | 189.8 | " | 4.821 | 1.130 | 20.52 | 189.8 |
| | 2 (Months) | " | 4.820 | 1.130 | 20.55 | 189.3 | " | 4.822 | 1.128 | 20.55 | 190.1 |
| | 4 (Months) | " | 4.818 | 1.131 | 20.56 | 189.2 | " | 4.186 | 1.131 | 20.35 | 188.2 |
| | 6 (Months) | " | 4.819 | 1.131 | 20.58 | 187.4 | " | 4.818 | 1.131 | 20.57 | 188.3 |
| SU-83003 | Beginning | " | 4.817 | 1.131 | 20.63 | 190.2 | " | 4.817 | 1.131 | 20.63 | 190.2 |
| | 2 (Months) | " | 4.819 | 1.132 | 20.63 | 190.2 | " | 4.817 | 1.130 | 20.52 | 188.4 |
| | 4 (Months) | " | 4.817 | 1.131 | 20.65 | 190.0 | " | 4.818 | 1.132 | 20.56 | 187.9 |
| | 6 (Months) | " | 4.816 | 1.132 | 20.66 | 187.8 | " | 4.816 | 1.132 | 20.58 | 186.9 |

TABLE 2

| Condition | Period | Lot No. SU-83001 | | | | | SU-83002 | | | | | SU-83003 | | | | |
|---|---|---|---|---|---|---|---|---|---|---|---|---|---|---|---|---|
| | | Result (Remarks) | pH | Density | Viscosity | Content | Result | pH | Density | Viscosity | Content | Result | pH | cosity | Vis- tent | Content |
| Direct Ray | Beginning | Suitability | 4.819 | 1.130 | 20.62 | 189.6 | Suitability | 4.821 | 1.130 | 20.52 | 189.8 | Suitability | 4.817 | 1.131 | 20.63 | 190.2 |
| | 1 Day | Suitability | 4.821 | 1.130 | 20.63 | 188.2 | Suitability | 4.818 | 1.132 | 20.49 | 190.4 | Suitability | 4.821 | 1.131 | 20.55 | 190.1 |

TABLE 2-continued

| | | Lot No. | | | | | | | | | | | | | |
|---|---|---|---|---|---|---|---|---|---|---|---|---|---|---|---|
| | | SU-83001 | | | | | SU-83002 | | | | | SU-83003 | | | |
| | | | | | | | Remarks | | | | | | | | |
| Condition | Period | Result | pH | Density | Viscosity | Content | Result | pH | Density | Viscosity | Content | Result | pH | Viscosity | Content |
| | 2 Days | Suitability | 4.817 | 1.131 | 20.61 | 188.9 | Suitability | 4.820 | 1.131 | 20.52 | 188.4 | Suitability | 4.818 | 1.132 | 20.64 | 189.1 |
| | 3 Days | Suitability | 4.818 | 1.131 | 20.64 | 188.2 | Suitability | 4.816 | 1.132 | 20.54 | 185.8 | Suitability | 4.817 | 1.132 | 20.64 | 187.7 |
| Scattering Ray | Beginning | Suitability | 4.819 | 1.130 | 20.62 | 189.6 | Suitability | 4.821 | 1.130 | 20.52 | 189.8 | Suitability | 4.817 | 1.131 | 20.63 | 190.2 |
| | 5 Days | Suitability | 4.816 | 1.130 | 20.63 | 189.5 | Suitability | 4.820 | 1.132 | 20.51 | 188.6 | Suitability | 4.820 | 1.132 | 20.61 | 188.9 |
| | 10 Days | Suitability | 4.819 | 1.131 | 20.64 | 188.6 | Suitability | 4.818 | 1.131 | 20.53 | 189.2 | Suitability | 4.817 | 1.132 | 20.63 | 189.3 |
| | 20 Days | Suitability | 4.822 | 1.130 | 20.62 | 189.6 | Suitability | 4.817 | 1.133 | 20.54 | 187.7 | Suitability | 4.818 | 1.132 | 20.65 | 188.4 |
| | 30 Days | Suitability | 4.817 | 1.131 | 20.63 | 187.2 | Suitability | 4.819 | 1.132 | 20.57 | 187.3 | Suitability | 4.816 | 1.133 | 20.64 | 187.8 |

TABLE 3

| | | Lot No. | | | | | | | | | | | | | | |
|---|---|---|---|---|---|---|---|---|---|---|---|---|---|---|---|---|
| | | SU-83001 | | | | | SU-83002 | | | | | SU-83003 | | | | |
| | | | | | | | Remarks | | | | | | | | | |
| Condition | Period | Result | pH | Density | Viscosity | Content | Result | pH | Density | Viscosity | Content | Result | pH | Density | Viscosity | Content |
| Long Period | Beginning | Suitability | 4.819 | 1.130 | 20.62 | 189.6 | Suitability | 4.821 | 1.130 | 20.51 | 189.8 | Suitability | 4.818 | 1.131 | 20.63 | 190.2 |
| | 3 (Months) | Suitability | 4.819 | 1.131 | 20.63 | 189.9 | Suitability | 4.820 | 1.131 | 20.52 | 189.7 | Suitability | 4.818 | 1.132 | 20.62 | 190.2 |
| | 6 (Months) | Suitability | 4.818 | 1.129 | 20.62 | 188.4 | Suitability | 4.811 | 1.132 | 20.56 | 190.2 | Suitability | 4.821 | 1.131 | 20.61 | 188.6 |
| | 9 (Months) | Suitability | 4.821 | 1.131 | 20.65 | 190.1 | Suitability | 4.818 | 1.129 | 20.55 | 188.6 | Suitability | 4.819 | 1.130 | 20.64 | 188.9 |
| | 12 (Months) | Suitability | 4.818 | 1.129 | 20.65 | 188.5 | Suitability | 4.816 | 1.131 | 20.54 | 187.7 | Suitability | 4.818 | 1.132 | 20.64 | 186.5 |
| | 18 (Months) | Suitability | 4.817 | 1.133 | 20.64 | 187.7 | Suitability | 4.817 | 1.132 | 20.54 | 186.9 | Suitability | 4.819 | 1.133 | 20.56 | 187.4 |
| | 24 (Months) | Suitability | 4.818 | 1.131 | 20.65 | 186.0 | Suitability | 4.816 | 1.131 | 20.57 | 185.0 | Suitability | 4.816 | 1.132 | 20.67 | 185.8 |

EXPERIMENT 2

1. Procedure

This method was designed to evaluate activity based on the oral administration of the pharmaceutical liquid from the Example 1 to animals. The animals used in this test were male and female Sprague Dawley rats who were 7-8 weeks old and weighted 220+20 g, and male and female Day mice who were 6-7 weeks old and weighed 20+2.0 g and 18+2.0 g, respectively. Before performing this test, the animals were fed solid feed stuffs at a temperature of 24°+2° C. and a moisture of 65+5%. 7 days prior to test initiation, the pharmaceutical liquid of the present invention was orally administrated to the animals. A group has 10 animals.

2. Results pharmaceutical liquid of the present invention are shown in Tables 4 (Rats) and 5 (Mice) as follows:

TABLE 4

| Sex | Dosage (ml/kg) | 1 (Day) | 2 (Days) | 3 (Days) | 4 (Days) | 5 (days) | 6 (Days) | 7 (Days) | Fetal % | $ID_{50}$ |
|---|---|---|---|---|---|---|---|---|---|---|
| Male | 15 | 0/10 | | | | | | | | |
| | 30 | " | | | | | | | | |
| | 45 | " | | | | | | | | |
| | 60 | " | | | | | | | | |
| | 75 | " | | | | 1/10 | | 1/10 | 10 | |
| Female | 15 | 0/10 | | | | | | 0/10 | | |
| | 30 | " | | | | | | " | | |
| | 45 | " | | | | | | " | | |
| | 60 | " | | | | | | " | | |
| | 75 | " | | | | | | " | | |

TABLE 5

| Sex | Dosage (ml/kg) | 1 (Day) | 2 (Days) | 3 (Days) | 4 (Days) | 5 (days) | 6 (Days) | 7 (Days) | Fetal % | $ID_{50}$ |
|---|---|---|---|---|---|---|---|---|---|---|
| Male | 70 | 0/10 | | | | 2/10 | | 2/10 | 20 | |
| | 80 | " | | | | 2/10 | | 3/10 | 30 | |
| | 90 | " | 1/10 | | 2/10 | | 5/10 | | 50 | |
| | 100 | " | 3/10 | 5/10 | | 7/10 | | 8/10 | 80 | |
| | 110 | " | 2/10 | 4/10 | 5/10 | 7/10 | 10/10 | 10/10 | 100 | 109.6 |
| Female | 70 | 0/10 | | | | | | | 0 | |

TABLE 5-continued

| Sex | Dosage (ml/kg) | 1 (Day) | 2 (Days) | 3 (Days) | 4 (Days) | 5 (days) | 6 (Days) | 7 (Days) | Fetal % | $ID_{50}$ |
|---|---|---|---|---|---|---|---|---|---|---|
| | 80 | " | | | 1/10 | | 2/10 | 2/10 | 20 | |
| | 90 | " | | 2/10 | | 4/10 | | 4/10 | 40 | |
| | 100 | " | 2/10 | 4/10 | 7/10 | | 8/10 | 8/10 | 80 | |
| | 110 | " | 3/10 | 5/10 | 8/10 | 9/10 | | 10/10 | 100 | 109.6 |

In the Table 5, the mice that were treated with a 110 ml/kg dosage were killed. However, the mice treated with $LD_{50}$ at 109.6 ml/kg of average dosage lived.

Accordingly, the results from Table 4 and 5 indicate suitable toxic activity with the pharmaceutical liquid of the present invention.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing a pharmaceutical liquid composition, which comprises the steps of:
   (a) extracting a first microparticle mixture of Dioscoreae Rhizoma, Glycyrrhizae Radix, Ginseng Radix, Typhae Pollen, Massa Medicata Fermentata, Sojae germinatum Semen, Cinnamomi Cortex, Paeoniae Radix, Liriope Tuber, Scutellariae Radix, Angelicae Gigantis Radix, Ledebouriellae Radix, Atractylodis Rhizome Alba, Bupleuri Radix, Platycodi Radix, Armeniacae Semen, Hoelen, Cnidii Rhizoma, Antellopis Cornu, Ampelopsis Radix, and Zingiberis Rhizoma and extracting said first microparticle mixture with water to provide a first extract and filtering said first extract to provide a first filtrate,
   (b) combining Bezoar Bovis, Moschus and Rhinocerotis with water to produce a Bezoar Bovis-water mixture,
   (c) combining Borneol with ethanol to produce a Borneol-ethanol mixture,
   (d) combining gelatin and water to produce a gelatin solution, and
   (e) combining said first filtrate, said Bezoar Bovis-water mixture, said Borneol-ethanol mixture and said gelating solution to produce said pharmaceutical composition.

2. The process of claim 1, wherein the Bezoar Bovis, Dioscoreae Rhizoma, Glycyrrhizae Radix, Ginseng Radix, Rhinocerotis Typhae Pollen, Massa Medicata Fermentata, Sojae germinatum Semen, Cinnamomi Cortex, Gelatin, Paeoniae Radix, Liriopsis tuber, Scutellariae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Moschus, Borneol, Ampelopsis Radix, Zingiberis Rhizoma, Cinnabaris, Realgar, Aurum, and Mel are present in an amount of about 14 parts, about 450 parts, about 320 parts, about 160 parts, about 150 parts, about 100 parts, about 100 parts, about 130 parts, about 130 parts, about 66 parts, about 110 parts, about 110 parts, about 110 parts, about 110 parts, about 120 parts, about 110 parts, about 80 parts, about 80 parts, about 80 parts, about 84 parts, about 180 parts, about 65 parts, about 18.75 parts, about 180 parts, about 46 parts, about 46 parts and about 23 parts, about 50 parts, about 26 parts, about 100 parts, by weight, respectively.

3. The process for preparing a pharmaceutical liquid composition of claim 1, wherein an aromatic agent, sweetening agent, emulsifier colloidal agent, suspension agent, and or preservative are further added to the pharmaceutical liquid composition.

4. The process for preparing a pharmaceutical liquid composition of claim 3, wherein the sweetening agent is ASPARTAME.

* * * * *